(12) United States Patent
Sauer et al.

(10) Patent No.: US 6,533,796 B1
(45) Date of Patent: Mar. 18, 2003

(54) LOADER FOR SURGICAL SUTURING INSTRUMENT

(75) Inventors: Jude S. Sauer, Pittsford, NY (US); John F. Hammond, Canandaigua, NY (US)

(73) Assignee: LSI Solutions, Inc., Victor, NY (US)

( * ) Notice: Subject to any disclaimer, the term of this patent is extended or adjusted under 35 U.S.C. 154(b) by 163 days.

(21) Appl. No.: 09/686,420

(22) Filed: Oct. 11, 2000

(51) Int. Cl.⁷ .............................................. A61B 17/04
(52) U.S. Cl. ....................................... 606/144; 606/148
(58) Field of Search ................................. 606/144, 145, 606/146, 139, 148, 222, 225, 232

(56) References Cited

U.S. PATENT DOCUMENTS

| | | | | |
|---|---|---|---|---|
| 5,431,666 A | * | 7/1995 | Sauer et al. ................. | 606/139 |
| 5,562,686 A | * | 10/1996 | Sauer et al. ................. | 606/144 |
| 5,766,183 A | * | 6/1998 | Sauer ........................... | 606/139 |
| 5,814,069 A | * | 9/1998 | Schulze et al. ............. | 606/148 |
| 6,042,601 A | * | 3/2000 | Smith .......................... | 606/139 |
| 6,197,035 B1 | * | 3/2001 | Loubens et al. ............. | 606/148 |
| 6,368,334 B1 | * | 4/2002 | Sauer ........................... | 606/144 |

* cited by examiner

Primary Examiner—A. Vanatta
(74) Attorney, Agent, or Firm—Stephen B. Salai, Esq.; Donna P. Suchy, Esq.; Harter, Secrest & Emery LLP

(57) ABSTRACT

A quick loader and associated method for a surgical suturing instrument of the type having at least one ferrule receiving chamber and a suture receiving passage, includes a loader body having a recess formed therein for receiving an end of a surgical suturing instrument, a seat adjacent the recess for releasably holding at least one ferrule-tipped end of a suture in the seat, the seat being aligned and adjacent to a ferrule receiving chamber in the suturing instrument when the instrument is positioned in the recess, for permitting the transfer of the ferrules from the seat on the loader into the ferrule receiving chamber.

10 Claims, 9 Drawing Sheets

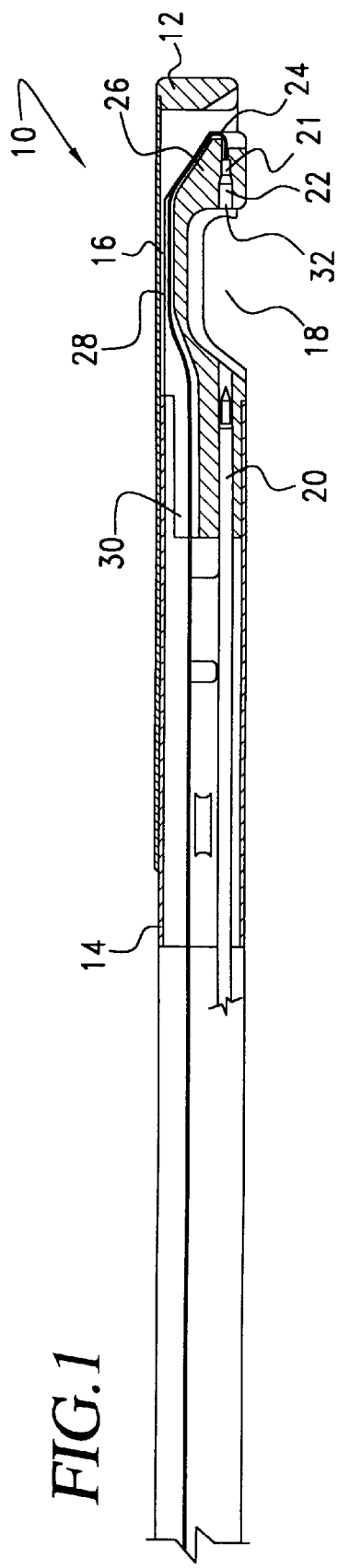
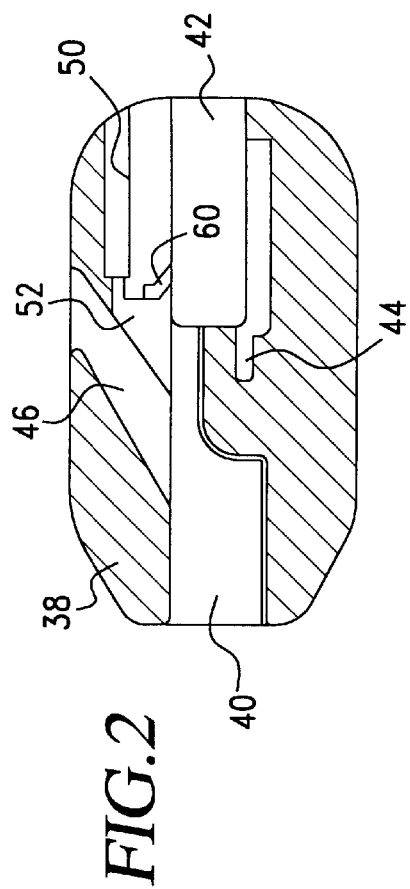

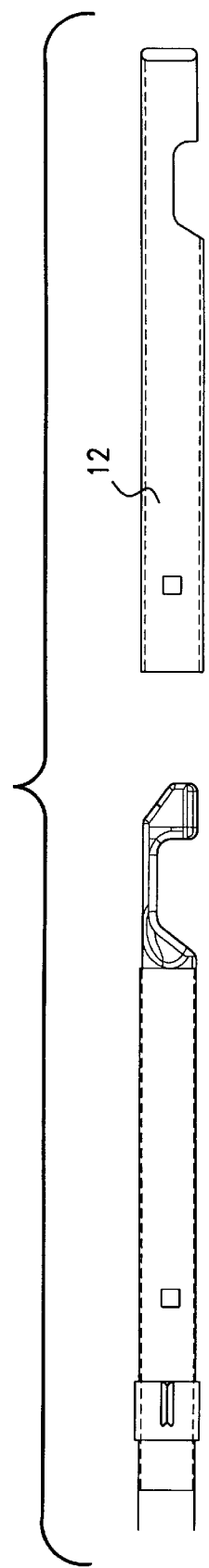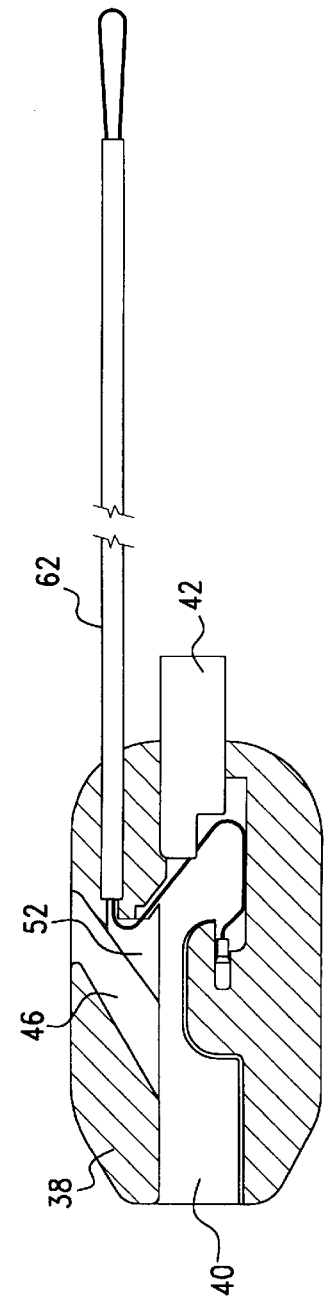

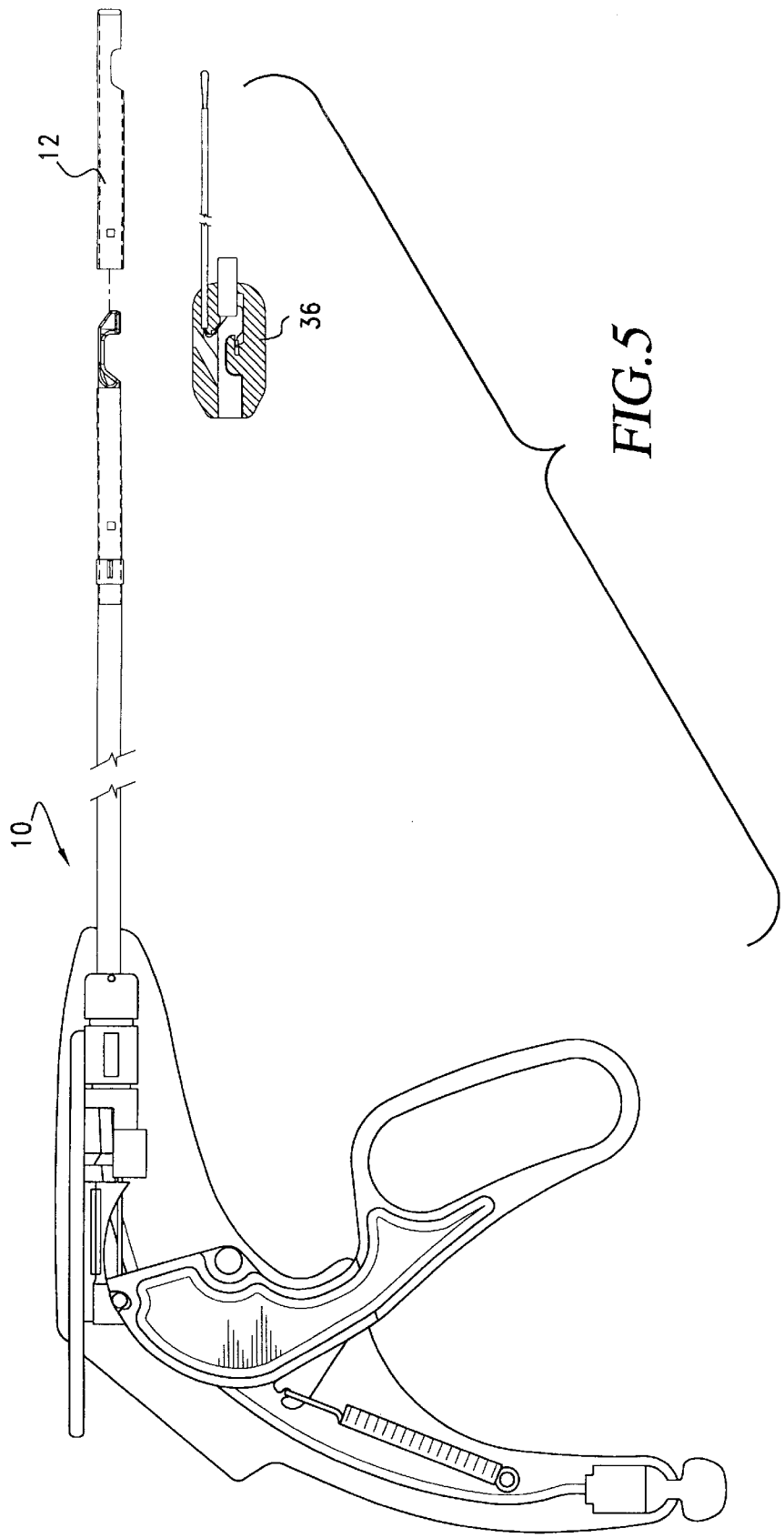

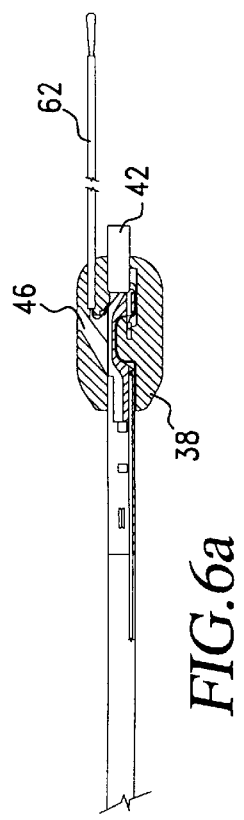
FIG. 6a
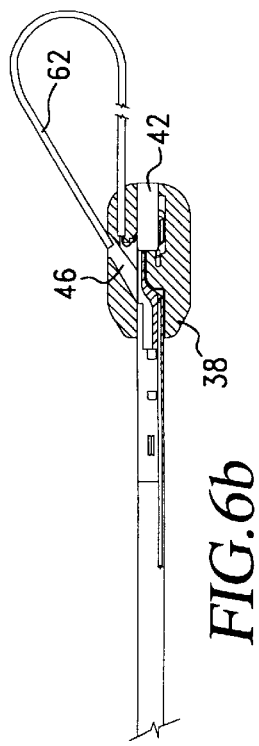
FIG. 6b
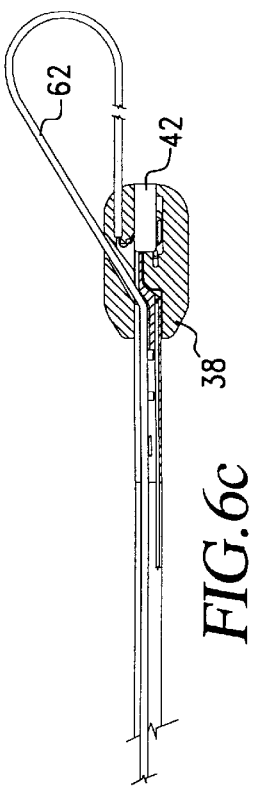
FIG. 6c
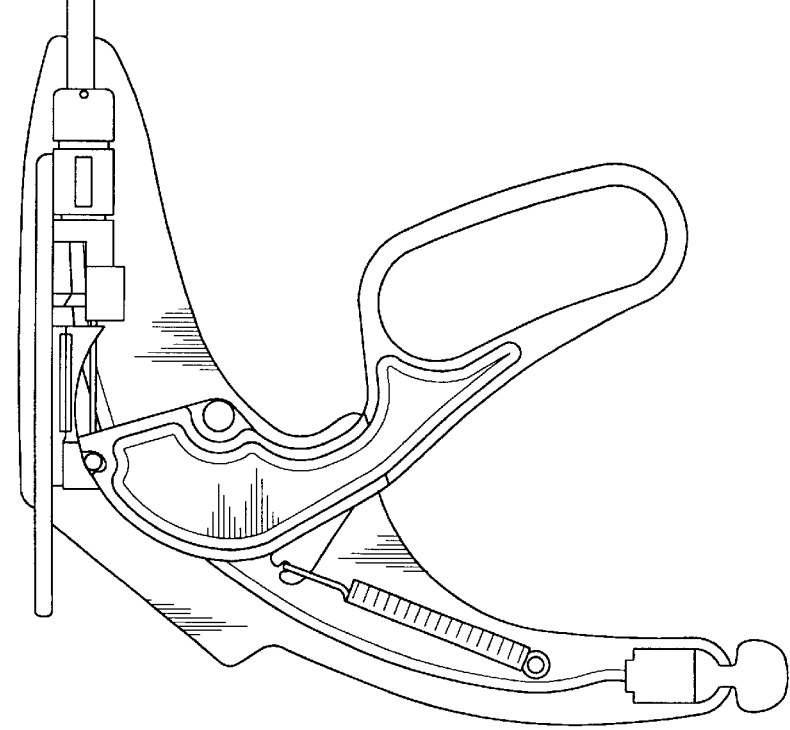

LOADER FOR SURGICAL SUTURING INSTRUMENT

FIELD OF THE INVENTION

This invention relates generally to surgical suturing instruments and more particularly to surgical suturing instruments of the type used to place and secure sutures having ferrules attached to the free ends thereof hereinafter "ferrule-tipped sutures" and more particularly to apparatus and a method for loading sutures into such instruments.

BACKGROUND OF THE INVENTION

Surgical suturing instruments have been developed that can place sutures remotely in laproscopic or endoscopic procedures. The instruments vary in construction but generally include a suturing tip located at the distal end of an elongated rigid or flexible shaft. The suturing tip has one or more needles, usually two, that can be passed across a gap through a tissue section, in a process sometimes referred to as "taking a bite," engage a ferrule-tipped suture end and pull the end back through the tissue section so that the suture engages the tissue. The process is repeated at a second location and the suture is secured to bring the tissue sections into apposition.

While surgical suturing instruments of the type just described are normally designed for disposal after use in a single procedure, they can be used multiple times during a procedure by reloading a new ferrule-tipped suture into the instrument and repeating the securing process.

Most commonly, the ferrule-tipped suture ends are disposed in cavities or recesses in the end of instrument and the center loop of suture material is disposed in a channel or passage in the instrument shaft and handle. Depending on the design of the instrument and the nature of the procedure in which it is used, the overall length of the ferrule-tipped suture may be several feet making it difficult or impossible to manually load a suture into a surgical suturing instrument.

SUMMARY OF THE INVENTION

Briefly stated and in accordance with a presently preferred embodiment of the invention, a quick loader for a surgical suturing instrument of the type having at least one ferrule receiving chamber and a suture receiving passage, includes a loader body having a recess formed therein for receiving an end of a surgical suturing instrument, a seat adjacent the recess for releasably holding at least one ferrule-tipped end of a suture in the seat, the seat being aligned and adjacent to a ferrule receiving chamber in the suturing instrument when the instrument is positioned in the recess, for permitting the transfer of the ferrules from the seat on the loader into the ferrule receiving chamber.

In accordance with another aspect of the invention, the loader includes a flexible tube having one end received in the loader body and holding a length of suture therein.

In accordance with still another aspect of the invention, the loader includes a channel in the loader body aligned with the suture receiving passage in the surgical suturing receiving instrument when the instrument is positioned in the recess to permit the entry of an end of the tube through the channel and into the suture receiving passage.

In accordance with still another aspect of the invention, the loader includes a slideable clip in the loader body for retaining the surgical suturing instrument in the recess.

A method for loading a suture into a surgical suturing instrument in accordance with this invention includes loading a center loop of a length of suture material into a flexible tube with the ends of the suture extending from one end of the tube, inserting the flexible tube into one end of a suture receiving passage in a surgical suturing instrument and out of a second end of the passage, and pulling the tube through the passage and off the center loop of the suture leaving the suture disposed in the passage.

In accordance with another aspect of the invention, a method for loading a suture in a surgical suturing instrument of the type having at least one ferrule-receiving chamber and a suture receiving passage includes the steps of positioning an end of the surgical suturing instrument in a chamber of a quick loader body carrying at least one end of a suture having a ferrule attached thereto in a seat aligned with and adjacent to the ferrule receiving chamber, inserting a flexible tube carrying a loop of the center loop suture into and through the suture receiving passage, withdrawing the flexible tube leaving the loop of suture in place in the suture receiving passage and transferring the ferrule-tipped end of the suture into the ferrule receiving chamber.

In accordance with another aspect of the method of this invention, the transferring step includes the step of pulling on the center of the suture loop for drawing the ferrule from the seat in the loader and into the aligned ferrule receiving chamber in the instrument to seat the ferrule in the ferrule receiving chamber.

The novel aspects of the invention are set forth with particularity in the appended claims. The invention itself together with further objects and advantages thereof may be more readily comprehended by reference to the following detailed description of a presently embodiment of the invention taken in conjunction with the accompanying drawing in which:

BRIEF DESCRIPTION OF THE DRAWING

FIG. 1 is a view, partly in section, of the end of a surgical suturing instrument of the type with which the loader of this invention is adapted to be used.

FIG. 2 is a section view of the body of a loader for a surgical suturing instrument in accordance with the invention.

FIG. 3 is an exploded view of the end of a surgical suturing instrument with the vacuum sleeve portion thereof detached.

FIG. 4 is a view, partly in section, of a suture loader in accordance with this invention.

FIG. 5 is an exploded view of a surgical suturing instrument, vacuum sleeve and suture loader ready for attachment to the instrument.

FIGS. 6 through 9 are sequential views showing a method for loading a suture into a surgical suturing instrument using the suture loader of this invention; and;

DETAILED DESCRIPTION OF THE INVENTION

Figure 7:
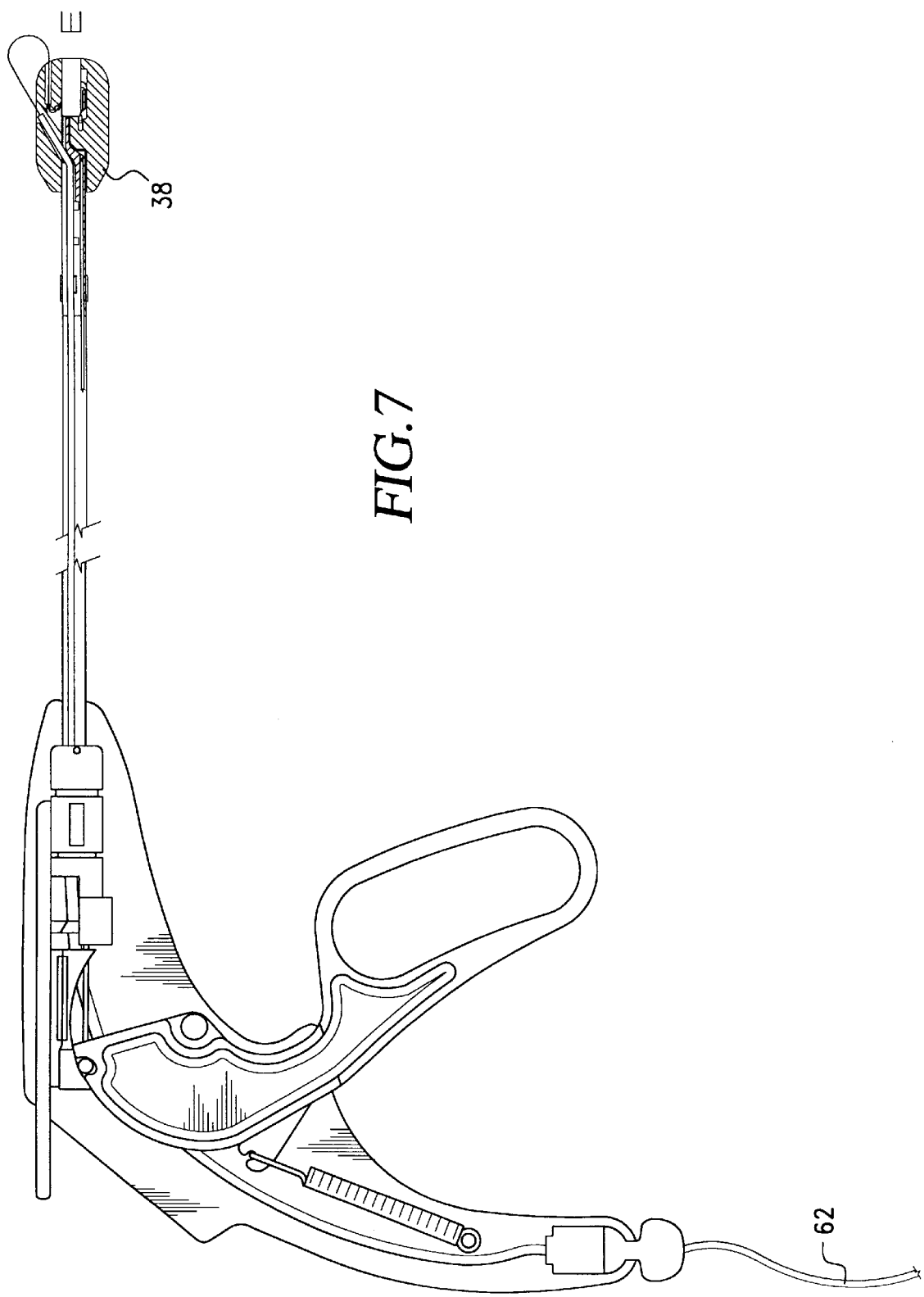

FIG. 1 is a section view of the distal end of a surgical suturing instrument of the type with which a suture loader in accordance with this invention can be used. The suturing instrument indicated generally at 10 has a vacuum sleeve 12 slideably mounted to the outside surface of a generally rigid cylindrical end tube 14. The operative portion of the suturing instrument 10 includes a C-shaped jaw 16 defining a gap 18 in which tissue to be sutured is positioned. The instrument includes a pair of needles 20 adjacent to the gap and disposed side by side so that only one is visible FIG. 1. The needles are operated to move through the gap 18 to engage a ferrule 21 attached to a free end 22 of a length of suture 24 and pull the ferrule-tipped suture through the tissue. A second ferrule is attached to the other end of the suture 24 but is not visible in FIG. 1.

A loop of suture extending between the ends affixed to the ferrules is wrapped around a bluntly pointed end 26 of the instrument and led through a groove 28 formed on the top of the jaw 16 opposite the gap 18 and then into a channel 30. The ferrule-tipped suture ends are received in a pair of cavities 32 only one of which is visible in FIG. 1. The ferrules 21 are relatively loosely retained in the cavities so that they may be easily extracted by the needles as will be described below. The ferrules 21 are held in the cavities 32 by tension on the suture ends, and may be reseated in the cavities by pulling on the center of the suture loop.

To operate the instrument, needle 20 is advanced through the gap 18 and through any tissue positioned therein until it engages ferrule 21. Preferably, the ferrule 21 has an oval or otherwise slightly out of round inner diameter that engages the tip of needle 20 and anchors the ferrule to the tip of 40 towards the closed end of the recess and then through a channel 60 into recess 52 and thence out through bore 50.

A flexible preferably plastic tube 62 whose overall length is slightly less than the length of the suture loop extending out of passage 50 is threaded over the suture loop. Tube 62 is frictionally held in bore 50 and the free end thereof is preferably coiled so that the loader, with a suture positioned therein can be provided in a compact package.

FIGS. 5 through 9 show a method for loading a suture into the surgical suturing instrument using the loader of this invention. FIGS. 10 through 15 are enlarged views of the end of the instrument with the suture loader positioned thereon as shown in FIGS. 5 through 9.

FIG. 5 shows the surgical suturing instrument 10, the sleeve 12 and the loader 36 as separate elements. The distal end of the surgical suturing instrument 10 is positioned in the recess 40 of the suture loader 36 as shown in FIG. 6a and the clip 42 is moved to a locking position as shown in FIG. 6b. The free end of the tube 62 is inserted through the channel 46 as shown in FIG. 6b and pushed into the groove 28 as shown in FIG. 6c. The tube passes through the surgical suturing instrument and out through a valve 62 located at the end of the instrument handle. The valve is preferably moved to an open position for allowing the tube to pass there through. FIG. 7 shows the instrument with the tube extending out a distal valve opening.

The tube 62 is gently pulled out of the bore 50 and along the length of the suture 24 through the suturing instrument 10, out through the valve 62 and then off the suture to release the suture loop.

Figure 8:
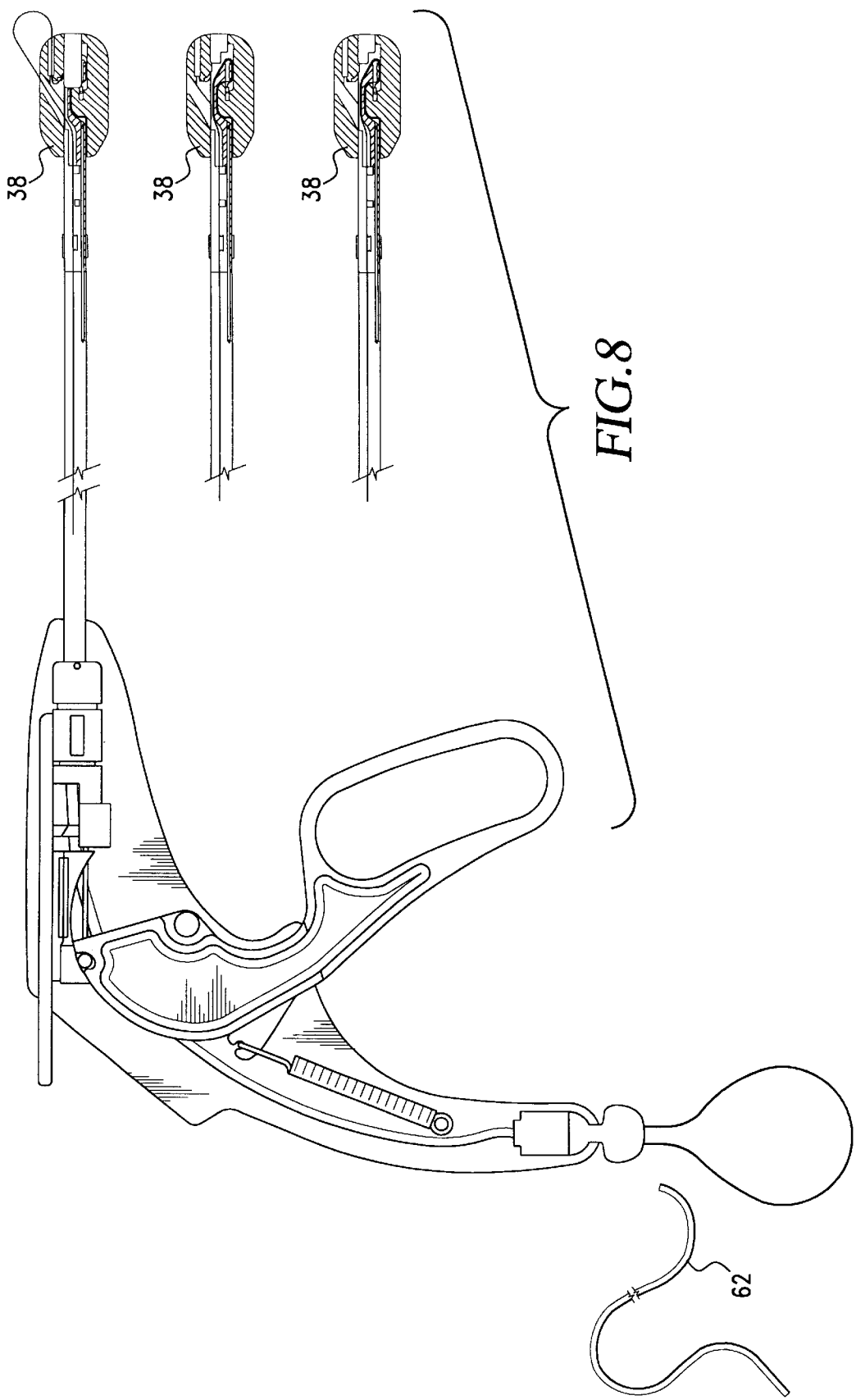
Figure 9:
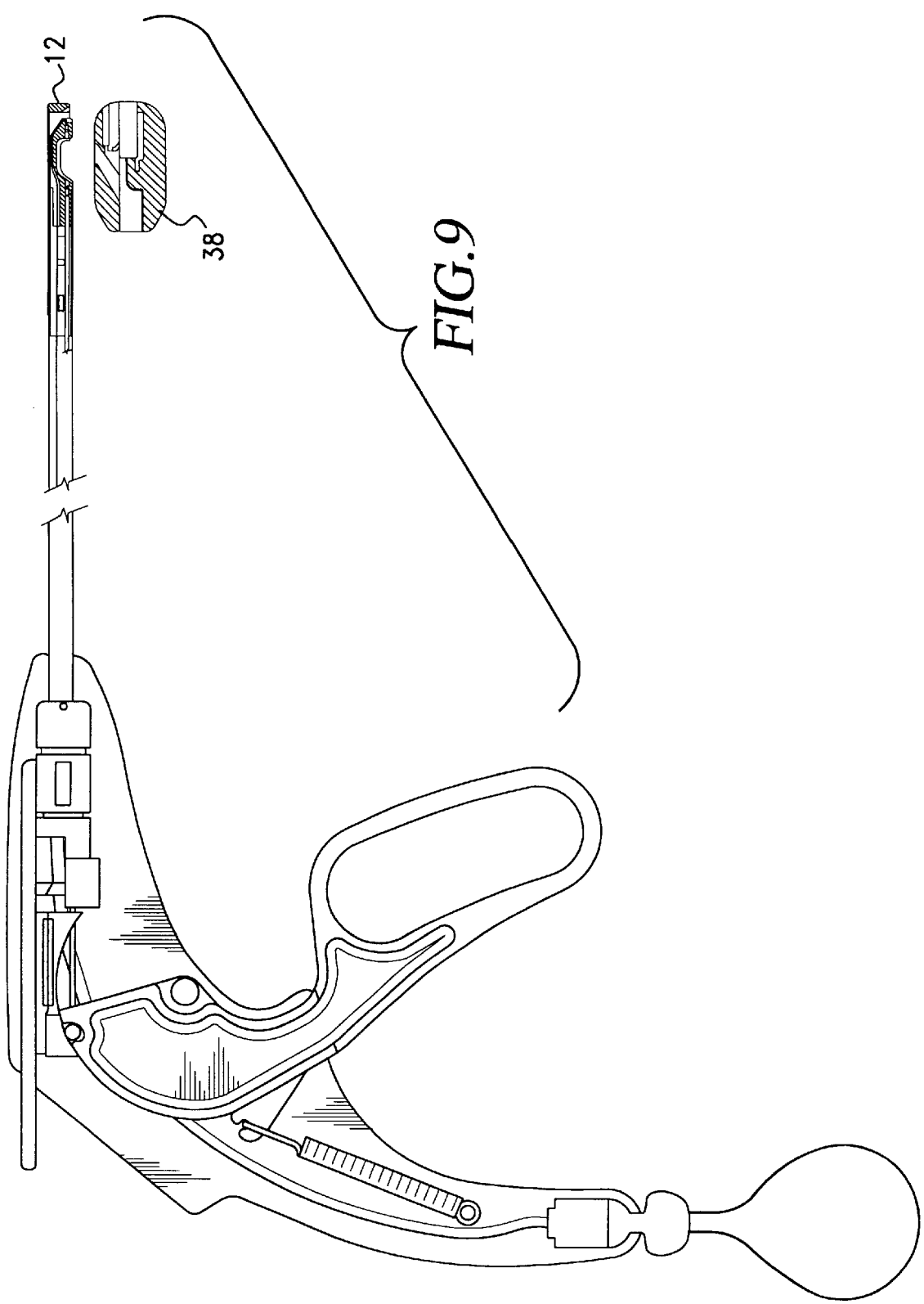
Figure 10:
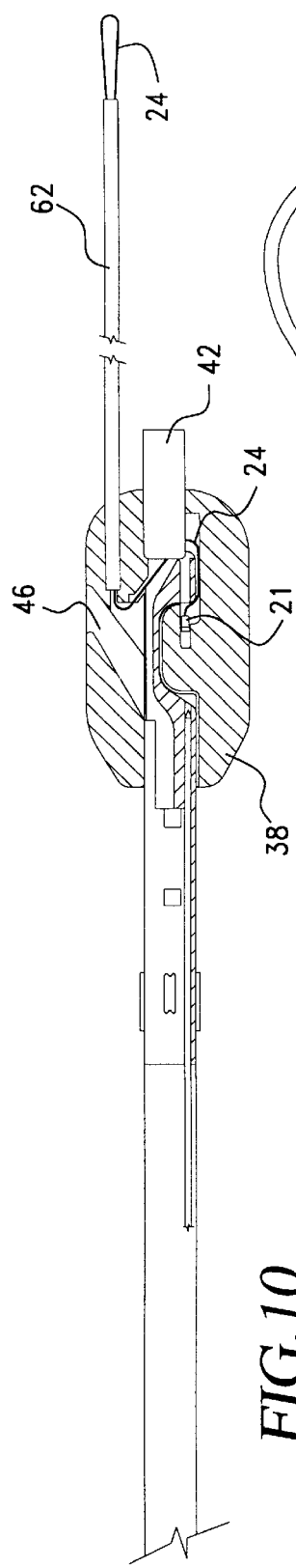
FIGS. 10 through 15 are enlarged views of the end of the surgical suturing instrument with the suture loader attached as shown in FIGS. 6 through 9.
Figure 11:
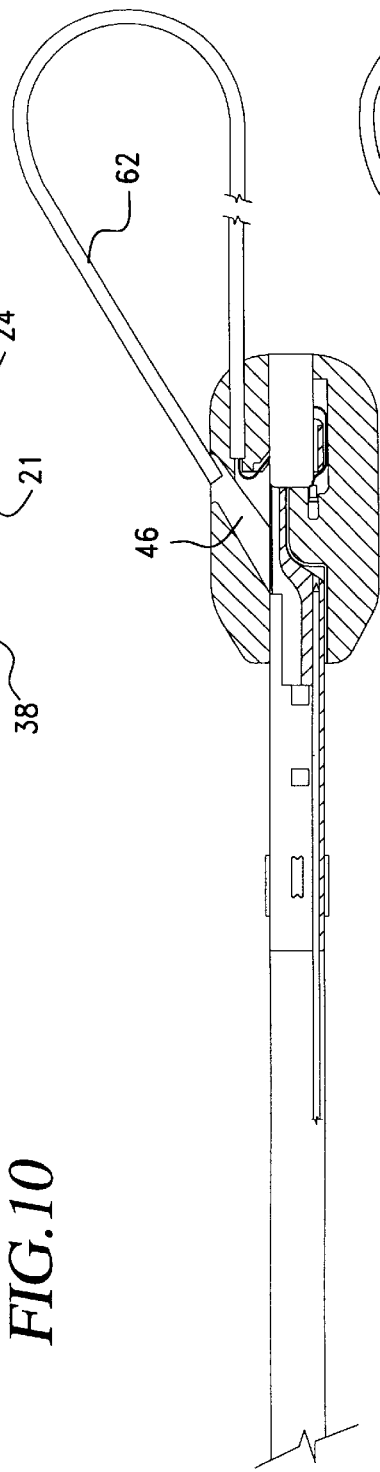
Figure 12:
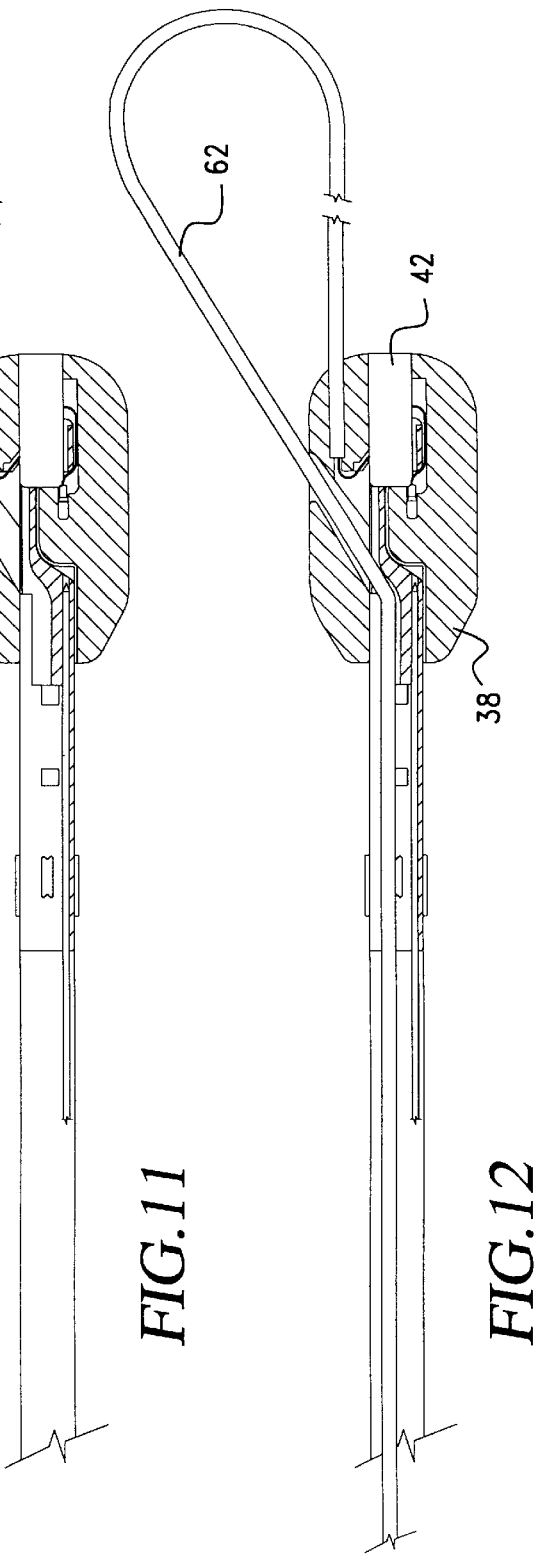
Figure 13:
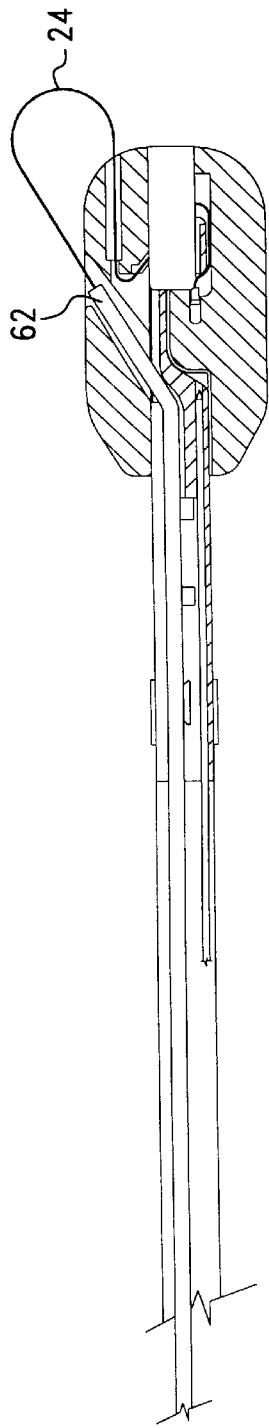
Figure 14:
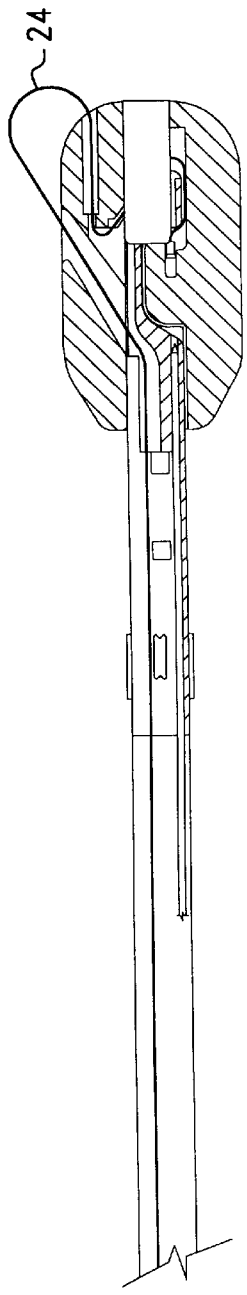
Figure 15:
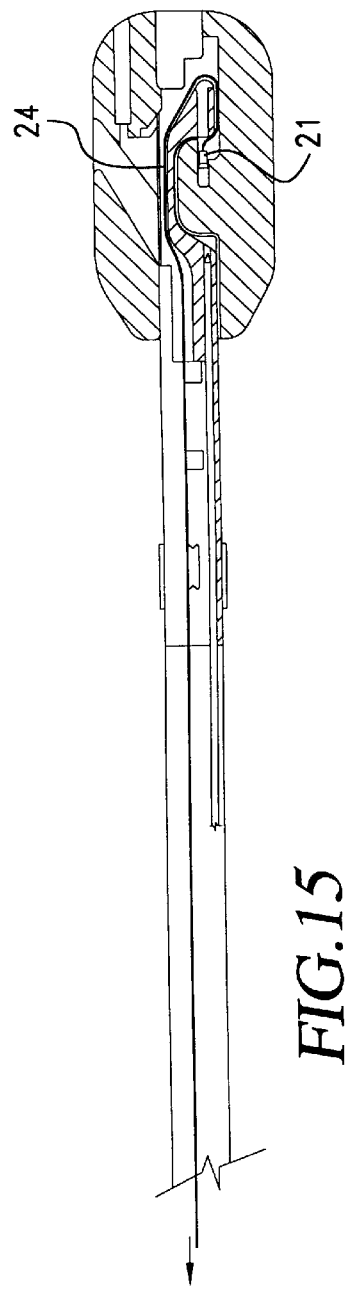

As shown in FIG. 8, the suture loop is pulled gently to pull the portion of the suture close to the ferrule fitted ends through a slot communicating bore 50 with recess 52 until the suture lies in the groove 28 on the top of the distal end of the instrument. At this point, the suture is trained around the end of the instrument and the ferrule-tipped ends of the suture are still in the seats in the suture loader. By applying more pressure to the suture loop that extends out the end of the handle of the instrument, the ferrule fitted ends of the suture are withdrawn from the seats in the loader and transferred into the cavities 32 in the distal end of the suturing instrument. Once the ferrule fitted ends of the suture are fully seated in the cavities in the instrument, the clip 42 is moved to the open position and the loader body 38 is removed from the end of the instrument as shown in FIG. 9.

FIGS. 10 through 15 are enlarged views of the loading operation shown and described in connection with FIGS. 6 through 9. Once the suture has been loaded into the instrument and the ferrule fitted ends seated in the cavities in the instrument tip, the vacuum sleeve 12 is reinstalled on the end of the instrument and the instrument is ready for use.

While the invention has been described in connection with the presently preferred embodiment thereof, those skilled in the art will recognize that certain modifications and changes may be made therein without departing from the true spirit and the scope of the invention which accordingly is intended to be defined solely be the appended claims.

What is claimed is:

1. A quick loader for a surgical suturing instrument of the type having at least one ferrule receiving chamber and a suture receiving passage, comprising:

a loader body having a recess for receiving an end of a suturing instrument;

a seat adjacent the recess for releasably holding at least one end of a suture having a ferrule attached thereto, the seat being aligned with and adjacent to the ferrule receiving chamber in the suturing instrument when the end of the instrument is positioned in the recess for permitting the transfer of the ferrule from the seat on the loader and into the ferrule-receiving chamber.

2. The quick loader of claim 1 comprising a flexible tube received in the loader body and holding a length of suture.

3. The quick loader of claim 2 comprising a channel in the loader body the channel being aligned with the suture receiving passage in the surgical suturing instrument when the instrument is in the recess to permit the entry of an end of the tube tough the channel and into the suture receiving passage.

4. The quick loader of claim 1 comprising a slidable clip on the loader body for retaining a surgical suturing instrument in the recess.

5. A method of loading a suture in a surgical suturing instrument of the type having at least one ferrule receiving chamber and a suture receiving passage, comprising the steps of:

positioning an end of the surgical suturing instrument in a chamber of a quick loader body carrying at least one end of a suture having a ferrule attached thereto in a seat aligned with and adjacent to the ferrule receiving chamber;

inserting a flexible tube carrying a loop of the suture into and through the suture receiving passage;

withdrawing the flexible tube, leaving the loop of the suture in place in the suture receiving passage; and transferring the end of the suture having a ferrule attached into the ferrule-receiving chamber.

6. The method of claim 5 in which the transferring step comprises pulling on the suture loop for drawing the ferrule from the seat and into the aligned ferrule receiving chamber to seat the ferrule in the ferrule receiving chamber.

7. The method of claim 5 comprising securing the quick loader body to the end of the surgical suturing instrument.

8. The method of claim 7 in which the securing step comprises sliding a clip on the quick loader body to a securing position.

9. The method of claim 5 comprising the additional step of removing the end of the surgical suturing instrument from the chamber of the quick loader body.

10. A method of loading a suture into a suturing instrument comprising the steps of:

loading a center loop of the suture into a flexible tube;

inserting the flexible tube into one end of a suture receiving passage in the suturing instrument and out a second end; and pulling the tube off of the center loop of the suture through the second end.

* * * * *

UNITED STATES PATENT AND TRADEMARK OFFICE
CERTIFICATE OF CORRECTION

PATENT NO. : 6,533,796 B1  
DATED : March 18, 2003  
INVENTOR(S) : Jude S. Sauer and John F. Hammond It is certified that error appears in the above-identified patent and that said Letters Patent is hereby corrected as shown below:

<u>Column 4,</u>
Line 38, please delete "tough" and insert -- through --.

Signed and Sealed this

Sixth Day of May, 2003

JAMES E. ROGAN  
*Director of the United States Patent and Trademark Office*